(12) United States Patent
Trentini

(10) Patent No.: US 8,394,424 B2
(45) Date of Patent: Mar. 12, 2013

(54) **TOPICAL PHYTOTHERAPEUTIC COMPOUND FOR THE TREATMENT OF HERPES BASED ON *UNCARIA TOMENTOSA* AND EXTRACTION PROCESS FOR OBTAINING A VEGETAL EXTRACT FROM *UNCARIA TOMENTOSA***

(75) Inventor: Anny Margaly Maciel Trentini, Pinhais (BR)

(73) Assignee: Herbarium Laboratorio Botanico Ltda. (BR)

( * ) Notice: Subject to any disclaimer, the term of this patent is extended or adjusted under 35 U.S.C. 154(b) by 0 days.

(21) Appl. No.: 12/778,481

(22) Filed: May 12, 2010

(65) Prior Publication Data

US 2010/0233299 A1   Sep. 16, 2010

Related U.S. Application Data

(62) Division of application No. 11/661,599, filed on Mar. 1, 2007.

(30) Foreign Application Priority Data

Sep. 1, 2004 (BR) ...................................... 0403688
Aug. 31, 2005 (BR) ............. PROT 015050000057-D

(51) Int. Cl.
   *A61K 36/00* (2006.01)
(52) U.S. Cl. ...................................................... 424/725
(58) Field of Classification Search ........................ None
    See application file for complete search history.

(56) References Cited

U.S. PATENT DOCUMENTS

2004/0076698 A1* 4/2004 Castillo et al. ................ 424/773

OTHER PUBLICATIONS

Canadian Office Action dated Apr. 19, 2011 concerning Canadian Patent Application No. 2,577,800.
Applicant's Response of Oct. 19, 2011 to Canadian Office Action dated Apr. 19, 2011 concerning Canadian Patent Application No. 2,577,800.
Canadian Search Report issued in the Canadian Equivalent of U.S. Appl. No. 11/661,599 (parent of present application), Mar. 1, 2007.

* cited by examiner

*Primary Examiner* — Melenie McCormick
*Assistant Examiner* — Randall Winston
(74) *Attorney, Agent, or Firm* — Cantor Colburn LLP

(57) ABSTRACT

The present invention concerns a phytotherapic compound for the treatment of herpes based on *Uncaria tomentosa* characterized by the presence of: (a) A therapeutically efficient amount of an Herbal Extract from *Uncaria tomentosa* (Willd) DC Rubiaceae, (b) a pharmaceutically acceptable vehicle, (c) at least one pharmaceutically acceptable excipient, and, (d) optionally, pharmaceutically acceptable adjuvants. It also concerns a process of extraction for obtaining the Herbal Extract from *Uncaria tomentosa* (Willd) DC Rubiaceae, active ingredient of the phytotherapic compound for the treatment of herpes of the present invention.

21 Claims, 7 Drawing Sheets

(A)

(B)

(A)

(B)

(A)

(B)

(A)

(B)

TOPICAL PHYTOTHERAPEUTIC COMPOUND FOR THE TREATMENT OF HERPES BASED ON *UNCARIA TOMENTOSA* AND EXTRACTION PROCESS FOR OBTAINING A VEGETAL EXTRACT FROM *UNCARIA TOMENTOSA*

CROSS REFERENCE TO RELATED APPLICATION

This application is a divisional of U.S. application Ser. No. 11/661,599, filed Mar. 1, 2007, which is incorporated herein by reference.

FIELD OF THE INVENTION

The present invention concerns a topical phytotherapic compound, based on an *Uncaria* spp extract, designed for the treatment of mucocutaneous Herpes simplex.

BACKGROUND OF THE INVENTION

The use of topical products in the treatment of the mucocutaneous Herpes simplex in immunocompetent patients is currently restricted to the utilization of antiviral drugs which inhibit the DNA polymerase in the cells infected by the virus, preventing its replication. Among the aforementioned antiviral drugs, the most important is the acyclovir family (pencyclovir, gancyclovir, valacyclovir); however, in some cases idoxuridine, trifluorotimidine, vidarabine and foscamet are indicated. In topical applications, acyclovir toxicity is particularly observed in cases of hypersensitivity. Furthermore, when systemically administering antiviral drugs, adverse reactions are frequent occurrences. Topical anti-inflammatory drugs can also be used as adjuvant agents in the treatment. It should be observed that in the conventional herpes treatment which is under discussion here, the drugs have a synthetic origin and their basic activity is antimicrobial.

The pertinent literature explains that the manifestations of recurrent lip herpes occur in 20-45% of the population, and that, regardless of ethnic group or geographic region, approximately 70% of over 40-year-olds have antibodies against the type 1 HSV virus. The recurrence frequency among the affected individuals varies from rare episodes up to 12 recurrences or more per year. After the primary infection, which usually occurs in childhood, the virus establishes a latent infection in the trigeminal ganglions. In immunocompetent individuals, the reactivations represent episodes of limited replication, disappearing in 10 days or so, regardless of any treatment. At this stage, however, the release of infecting viral particles occurs, and they are likely to be contagious. The increasing use of topical antiviral drugs with activity on the DNA polymerase, such as the nucleoside analogs (acyclovir and pencyclovir), has been regarded as a reference for comparative studies. Although the reference treatment is generally safe, its clinical efficacy is limited, and there is an increasing concern about the emergence of a viral resistance due to the disseminated use of such cytostatic drugs, particularly in populations of immunocompromised individuals. Forecasts derived from mathematical models suggest that the increasing utilization of nucleoside analogs may raise the prevalence of resistant viral forms from the current 0.3% to 1.5-3.0% in the next 50 years. This possibility could represent an exponentially increasing dissemination of resistant viral forms. On the other hand, the topical drug anti-inflammatory activity itself helps to decrease the viral spreading by decreasing the intensity and duration of the symptoms of the active stage, in which the infection is likely to occur.

Among the most recent approaches to the treatment of inflammations caused by the herpes virus, phytotherapy, also referred to as herbal medicine, has been increasingly employed. One of the most promising plants is *Uncaria tomentosa*, colloquially known as "unha de gato" in Brazil, and, in other countries, as cat's claw, una de gato, paraguayo, garabato, garabato casha, samento, toron, tambor huasca, una huasca, una de gavilan, hawk's claw, saventaro.

The *Uncaria tomentosa* portions most used for phytotherapic purposes are the bark, roots and leaves. The traditional methods of manipulation of these portions for obtaining their therapeutically active components involve grinding, coction and extraction by means of solvent substances, with an optional heating.

*Uncaria tomentosa* belongs to the Rubiaceae family, formed by the main species *U. tomentosa* and *U. guianensis*. It has been used for centuries by Indians and the Amazonian forest populations for treating asthma, inflammations of the urinary tract, postpartum recovery, kidney infections, arthritis, rheumatism, gastric ulcers, cancer, and diabetes, among other illnesses. This fact suggests that *U. tomentosa* contains a wide range of therapeutic and prophylactic components. In relatively recent years the ethnologist Klaus Keplinger offered a decisive contribution for the elucidation of the *U. tomentosa* compound and its potential strength as a phytotherapic agent, inclusively for the treatment of cancer and AIDS, according to the patents U.S. Pat. No. 4,844,901, U.S. Pat. No. 4,940,725, U.S. Pat. No. 5,302,611, and U.S. Pat. No. 5,723,625. Keplinger's work has been amplified by contributions from other researchers, who have taken ahead the task of elucidating the components' potential phytotherapic activity and determining how they can be put to use.

The chemical compound of *U. tomentosa* includes 17 different alkaloids, glycosides of the quinovic acid, tannins, flavonoids, steroid fractions, including sitosterol, sigmasterol and carpesterol, triterpenes and other compounds (Sentore A, Cataldo A, Iaccarino F, et al. Phytochemnical and biological research on *Uncaria tomentosa* L. Boll Soc Ital Biol Sper 1989; 65:517-520). The "James Duke's Phytochemnical and Ethnobotanical" database presents a list of 29 chemical constituents present in *Uncaria tomentosa* (Beckstrom-Sternberg S, Duke J, Wain K. Chemicals in: *Uncaria tomentosa* DC (Pedaliaceae). 1994: The Ethnobotany Database, Agricultural Research Service). The following active constituents are particularly notable: the tetracyclic oxindole alkaloids (TOAs), represented by the compounds rynchophylline, isorynchophylline, corynoxeine, and isocorynoxeine (Keplinger et al., 1999 (Keplinger K, Laus G, Wurm M, et al. *Uncaria tomentosa* (Willd.) DC-Ethnomedicinal use and new pharmacological, toxicological and botanical results. J Ethnopharmacol 1999; 64:23-34); Laus G, Brossiner D, Keplinger K. Alkaloids of Peruvian *Uncaria tomentosa*. Phytochemistry; 45(4):855-860), 1997); Wagner H, Kreutzkamp B, Jurcic K. The alkaloids of *Uncaria tomentosa* and their phagocytosis-stimulating action [in German]. Planta Med 1985b October; (5):419-23). The most frequently investigated active constituents, which present immunomodulator and anti-inflammatory effects, are the pentacyclic oxindole alkaloids (PDAs). The already characterized POAs are: pteropodine, uncarine C, isopteropodine, uncarine E, speciophylline, uncarine F, Mitraphyllinee, and isoMitraphyllineee (Muhammad et al., 2001a (Muhammad I, Khan I A, Fischer N H, Fronczek F R. Two stereoisomeric pentacyclic oxindole alkaloids from *Uncaria tomentosa*: uncarine C and uncarine E. Acta Cryst 2001a; C57:240-2); Laus et al., 1997; Wagner et al., 1985b;

Stuppner H, Sturm S, Konwalinka G. HPLC analysis of the main oxindole alkaloids of *Uncaria tomentosa*. Chromatographia 1992; 34:597-600).

*Uncaria tomentosa* has got two chemotypes: (1) the pentacyclic alkaloids type, and (2) the tetracyclic alkaloids type. The first one, which contains pentacyclic oxindole alkaloids (PDAs), is regarded by some researchers as the most active component of the cat's claw plant and contains just a few—or even none—tetracyclic oxindole alkaloids (TOAs). The second chemotype contains predominantly TOAs, both with no POAs at all and with a considerable amount of POAs. The TOAs are believed to be POAs antagonists on what concerns to the POAs' desirable effects, and, therefore, it is important to tell the two chemotypes from one another (Wurm M, Kacani L, Laus G, Keplinger K, Dierich M. Pentacyclic oxindole alkaloids from *Uncaria tomentosa* induce human endothelial cells to release a lymphocyte-proliferation-regulating factor. Planta Med 1998; 64:701-704).

Thus, the determination of the chemotype is crucially important in the plant's analysis and processing, with the purpose of obtaining a pharmaceutical preparation. This is due to the fact that the pentacyclic and tetracyclic alkaloids possess different activity mechanisms, and as previously mentioned, they may even be antagonists to each other (Keplinger, K., Laus, G., Wurm, M. et col.: *Uncaria tomentosa* (Willd.) DC. —ethnomedicinal use and new pharmacological, toxicological and botanical results. J Ethnopharmacol, 1999, 64: 23-34; Reinhard K. H.: *Uncaria tomentosa* (Willd.) DC. —Cat's claw, Una de gato oder Katzenkralle. Z. Phytother, 1997, 18: 112-121).

The document FR 2824270 describes a process of preparation of a hydroalcoholic extract from *Uncaria tomentosa* (Example 1, b1-a), in which finely sectioned portions of the plant are subject to reflux, at a temperature of 65.degree. C., for 2 hours, in a 70% ethanol aqueous solution. This process presents some disadvantages, such as: (i) heating favors isomerization and other alterations in the physical-chemical characteristics of the constituents found in the in natura plant, and (ii) the chemical non-characterization and non-standardization of the extract obtained prevents the control of the final product's therapeutic activity. As a matter of fact, the compound described in the document FR 2824270 has got a predominantly cosmetic purpose.

Pharmacological studies have shown that the pentacyclic oxindole alkaloids, active constituents of the herbal extract of the plant *Uncaria tomentosa* (Willd) DC Rubiaceae, present immunomodulator anti-inflammatory, antioxidant and cytoprotective activities. The quinovic acid glycosides present in *Uncaria tomentosa* have been tested in cell cultures (CER and HeLa), showing antiviral and anti-inflammatory activity. The mutagenic and antimutagenic potential of *Uncaria tomentosa* presents antimutagenic activity in photomutagenic systems in vitro and absence of mutagenic effect in *Salmonella typhimurium*. Experimentally, *Uncaria tomentosa* could offer protection against a whole range of oxidative stresses, including the peroxynitrite, which has been implied as a mediator in the arthritis inflammation and other chronic inflammatory diseases, as well as against the cytotoxicity induced by UV rays and free radicals. The anti-inflammatory effect of *Uncaria tomentosa* results from its ability of inhibiting the production of TNF-alfa in vitro and in vivo and, in a smaller extent, of PGE2, both of them mediators of the inflammatory processes. The expression of the NF-kappaB transcription factor, which regulates the transcription of several genes involved in the inflammatory process, is reduced in vitro by *Uncaria tomentosa* extracts. On the other hand, its immunomodulator effect has been attributed to the increase in the lymphocites' proliferative ability, the stimulation of the phagocitary activity and the increase in the IL-1 and IL-6 production. Studies of the preclinical toxicity of the *Uncaria tomentosa* extracts have not shown any toxicity in vitro in concentrations up to 100 mg/ml.

Two tests (uncontrolled; unpublished results) with the extract of *U. tomentosa*-POA in topical preparations to be used in lesions caused by Herpes simplex and Varicela zoster have been performed, with better outcomes and with no adverse side effects (Immodal Pharmaka. Krallendorn® *Uncaria tomentosa* (Willd.) DC Root Extract: Information for Physicians and Dispensing Chemists. 3rd revised ed. Volders, Austria:Immodal; 1995. Available on request from immodal@volders.netwing.at. Immodal Pharmaka. Radix Uncariae tomentosae (Willd.) DC., pentacyclic chemotype (Krallendorn®): summarized research. Volders, Austria; Immodal. 2002. Immodal Pharmaka. Summary and assessment of clinical examinations of Krallendorn® products. Volders, Austria: Immodal, 1999a, Available on request from immodal@volders.netwing.at.; Immodal Pharmaka. Summary and assessment of: Pharmacodynamical examinations of extracts of *Uncaria tomentosa* (Willd.) DC. mod. pent. Volders, Austria: Immodal; 1999b).

In Western Europe the *U. tomentosa* extracts are used in daily doses of approximately 20-60 mg of the dry extract. The POAs are poorly soluble in water and well soluble in acids and alcohols; therefore, the *U. tomentosa* extracts are prepared in the form of 50% hydroalcoholic tinctures. In Germany and Austria the *U. tomentosa* extract in the form of a standardized powder is used two or three times a day in doses of 20-60 mg. Also in those two countries the preparations made from *U. tomentosa* roots are used mainly in disorders of the immune system (including allergies and rheumatoid arthritis) and as a supportive therapy to the treatment of cancer (to alleviate the consequences of chemotherapy and radiotherapy), as well as an adjuvant in viral infections with herpes or retroviruses as the HIV (Falkiewicz, B., ukasiak, J. "Vilcacora [*Uncaria tomentosa* (Willd.) DC. and *Uncaria guianensis* (Aublet) Gmell.]—a review of published scientific literature. Case Rep Clin Pract Rev, 2001: 2(4): 305-316).

In the United States market 4 types of *Uncaria* products are commercialized by 3 different manufacturers: (1) hydroalcoholic extract from *U. tomentosa* standardized for POAs; (2) aqueous extract from *U. tomentosa* standardized for CAES; (3) aqueous extract from *Uncaria guianensis* and (4) a relatively generic cat's claw product (usually labeled as UT), made from the plant's bark and roots, both in form of powder for capsules and tablets and finely sliced to be used in the form of tea (CAT'S CLAW (VINCARIA) *Uncaria tomentosa* (Willd.) DC.; *Uncaria guianensis* (Aubl.) Gmel. [Fam. Rubiaceae]-Overview; available in the Web in (http://www.sunrisewd.com/products/catsclawarticle.htm).

Although processes of extraction of pharmaceutically active components, including the hydroalcoholic extraction of *U. tomentosa* are already known, and, in addition to that, products designed for the treatment of herpes exist in the market, such products do not totally comply with the requisites of a satisfactory relief of the pain associated with the inflammation caused by the herpes virus and of a satisfactory bioavailability (for instance, a sufficient topical absorption) of the active components of *U. tomentosa*, especially the POAs.

SUMMARY OF THE INVENTION

The present invention aims at providing a topical phytotherapic compound for the treatment of herpes, designed to address the deficiencies of the compounds known in the art; such compound is to be prepared with an herbal extract from the plant *Uncaria tomentosa* (Willd) DC Rubiaceae, standardized in Mitraphylline.

Compared to the conventional products, the compound provided by the present invention possesses the main advantage of not fostering a viral resistance. While the synthetic or semisynthetic drugs currently in use present antimicrobial activity, the present compound exerts an immunomodulator and anti-inflammatory action, increasing the organic resistance itself and not interfering in the viral replication. Compared to the compounds based on *Uncaria* known to the technical state for the treatment of herpes, the compound of the present invention features an efficient action on the pain associated with the inflammation caused by HSV.

In a first concretization of the present invention, a phytotherapic compound for the treatment of herpes based on *Uncaria tomentosa* is provided, characterized by the presence of: (a) a therapeutically efficient amount of an Herbal Extract from *Uncaria tomentosa* (Willd) DC Rubiaceae, (b) a pharmaceutically acceptable vehicle, (c) at least one pharmaceutically acceptable excipient, and, (d) optionally, pharmaceutically acceptable adjuvants.

A second concretization of the invention concerns a process of extraction for obtaining a herbal extract from *Uncaria tomentosa*, characterized by including the following stages: (a) preparing a finely sliced material from portions of the standardized *Uncaria tomentosa* plant; (b) mixing the stage (a) material with a 70% ethanol aqueous solution and performing the turbolysis at room temperature for a period of time sufficient for extracting the active constituents; (c) separating the liquid phase containing the desired active constituents; (d) filtering the liquid obtained in the stage (c) for removing the remaining solid or semisolid particles; (e) optionally, repeating at least once the stages (a) through (d) for eliminating all solid materials from the desired active constituents, and (0 obtaining the *Uncaria tomentosa* tincture by mixing the fractions resulting from the extractions performed during the stages (a) through (d).

In a third concretization a phytotherapic compound for the treatment of herpes based on *Uncaria tomentosa* is provided, characterized by the presence of: (a) a therapeutically efficient amount of an Herbal Extract from *Uncaria tomentosa* (Willd) DC Rubiaceae, prepared by means of a process of extraction, which results in a plant extract from *Uncaria Tomentosa* (Willd) DC Rubiaceae, described in the present invention, (b) a pharmaceutically acceptable vehicle, (c) at least one pharmaceutically acceptable excipient, and, (d) Optionally, pharmaceutically acceptable adjuvants.

DETAILED DESCRIPTION OF THE INVENTION

Figure 1:
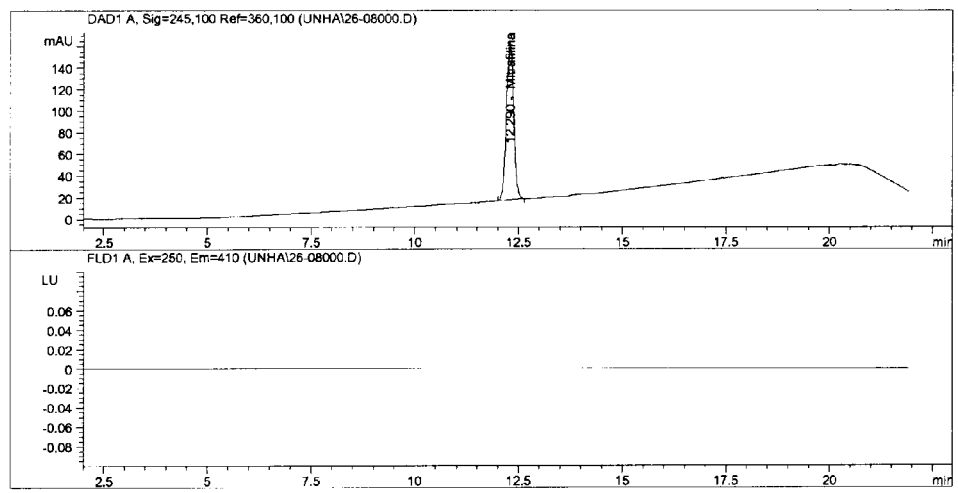
FIG. 1 shows the chromatogram (A) and the spectrum (B) of the Mitraphylline standard ($t_r$=12.290), one of the pentacyclic oxindole alkaloids.
Figure 1:
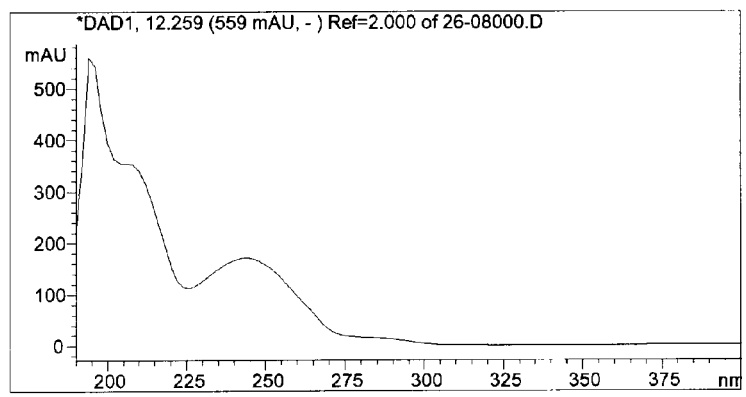
Figure 2:
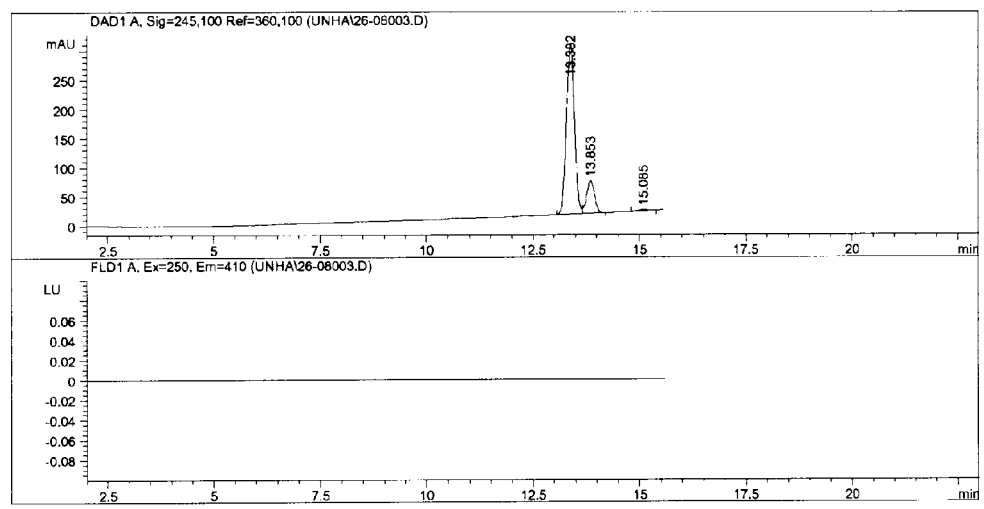
FIG. 2 shows the chromatogram (A) and the spectrum (B) of the IsoMitraphyllinee standard ($t_r$=13.382), another pentacyclic oxindole alkaloid. It is worth noting that the eluated peak next to the IsoMitraphyllinee (13.382), in the standard, is the isomeric impurity of approximately 15% of Uncarine C, information included in the Chromadex certificate of analysis.
Figure 2:
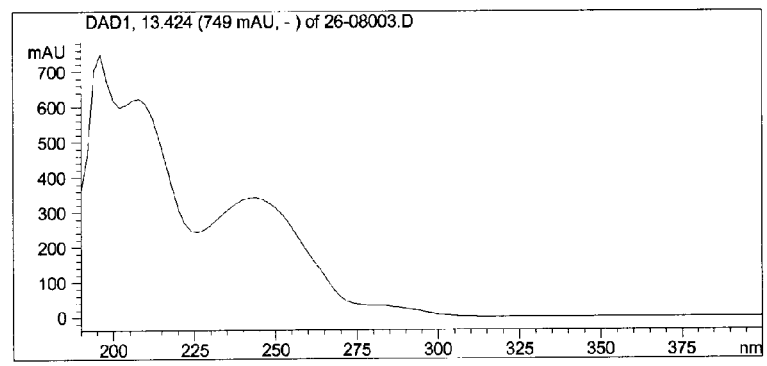
Figure 3:
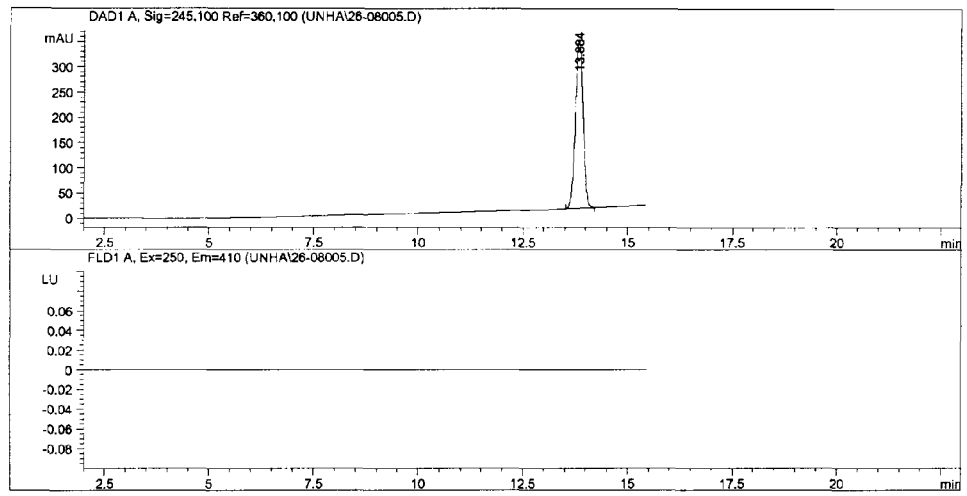
FIG. 3 shows the chromatogram (A) and the spectrum (B) of the Uncarine C standard ($t_r$=13.834), another pentacyclic oxindole alkaloid.
Figure 3:
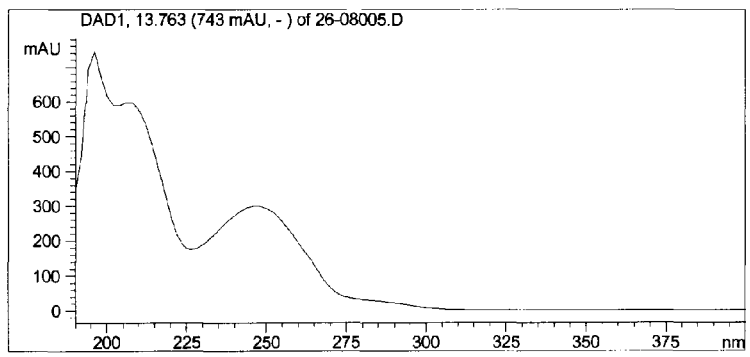

For the purpose of the present invention, some definitions are provided below:

Herbal extract from *Uncaria tomentosa* (Willd) DC Rubiaceae—means a hydroalcoholic mixture of *Uncaria tomentosa* powder, standardized in pentacyclic oxindole alkaloids calculated in Mitraphylline and characterized by a spectral profile. The extract's (a) organoleptic characteristics are: the aspect of a slightly turbid liquid, with the acrid odor characteristic of *Uncaria* and a reddish brown color, (b) physical-chemical characteristics are: (i) dry residue: 2.95-5.23%, (ii) pH: 5.0-5.5, (iii) density: 0.862-0.982 g/ml, (iv) content of total pentacyclic oxindole alkaloids, calculated as Mitraphylline: 660 µg/g-900 µg/g, and (v) identification by thin layer chromatography with bands in Rfs close to 0.7-0.8 and 0.25-0.3 related to the alkaloids.

POAs-term related to the pentacyclic oxindole alkaloids (PDAs) present in several portions of the *Uncaria tomentosa* plant, especially the root and bark. The POAs include: pteropodine, uncarine C, isopteropodinie, uncarine E, speciophylline, uncarine F, Mitraphyllinee, and isoMitraphyllineee.

As previously mentioned, the constitution of the *Uncaria tomentosa* extract depends, in a great extent, on the process used. This fact derives mainly from the differentiated solubility of the components present in the several portions of the plant, such as the root, bark and leaves, which are distributed over different chemical classes of compounds. For instance, the POAs are less soluble in water than the TOAs are.

In the present invention, the herbal extract from *Uncaria tomentosa* (Willd) DC Rubiaceae is obtained by means of a hydroalcoholic extraction process under strictly controlled conditions which ensures the preservation of the chemical structure and biological activity of the components present in the plant.

In a preferred concretization, the herbal extract from *Uncaria tomentosa* (Willd) DC Rubiaceae is obtained by means of an extraction process which includes the following stages: (a) preparing a finely sliced material from portions of the standardized *Uncaria tomentosa* plant; (b) mixing the stage (a) material with a 70% ethanol aqueous solution and performing the turbolysis at room temperature for a period of time sufficient for extracting the active constituents; (c) separating the liquid phase containing the desired active constituents; (d) filtering the liquid obtained in the stage (c) for removing the remaining solid or semisolid particles; (e) optionally, repeating at least once the stages (a) through (d) for eliminating all solid materials from the desired active constituents, and (f) obtaining the *Uncaria tomentosa* tincture by mixing the fractions resulting from the extractions performed during the stages (a) through (d). This process ensures the preservation of the physical-chemical characteristics of the phytocomplex, minimizing the occurrence of possible alterations caused by more severe conditions, such as heating, which frequently results in the formation of isomers and the consequent decrease in the extract's phytotherapic activity.

The finely sliced material utilized in the stage (a) of the process should preferably be in the form a powder obtained by the fragmentation of the plant's portions, preferentially the root, bark and/or leaves. On the stage (b) the *Uncaria tomentosa* material, finely sliced, is mixed with a 70% ethanol aqueous solution (with the pH corrected to 4.5 by the addition of organic acid) and subject to agitation, by turbolysis, for a preferential period of time of about 1 hour. The separation of the liquid phase in the stage (c) is preferably performed by centrifugation at, for instance, 60 Hz. The filtration, in the stage (d), is performed by an appropriate filtering system, such as depth filtration or filter press.

The stages (a) through (d) should preferably be repeated several times to ensure the maximal removal of the desired constituents present in the in natura plant. More preferentially, at least two extractions should be performed. More preferably yet, at least three extractions should be made.

The extract obtained by such process is a reddish liquid which contains an amount of total alkaloids, calculated as Mitraphylline, of about 660 µg-900 µg.

Figure 5:
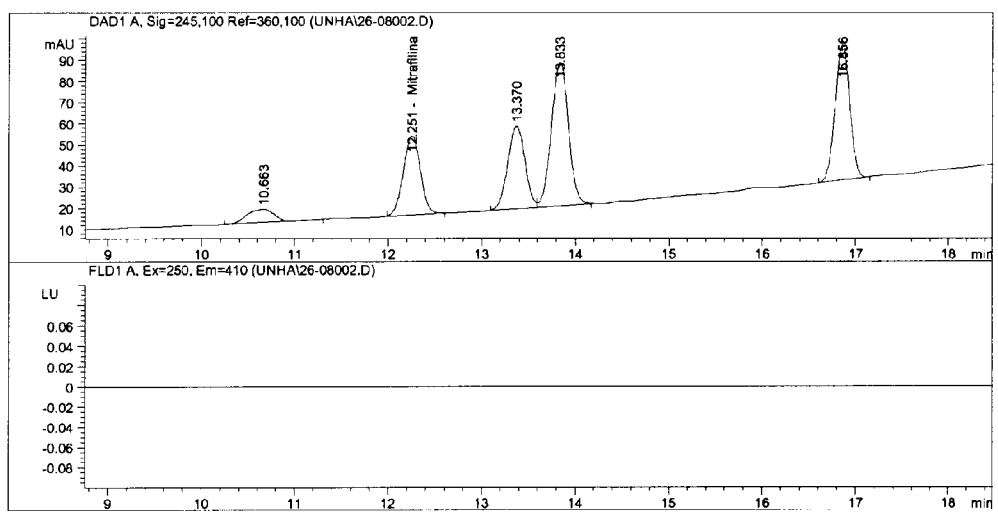
FIG. 5 shows: (A) the chromatogram of the *Uncaria Tincture*, the active ingredient of the compound in the present invention; and the spectrums of its constituents: (B) Uncarine F, (C) Mitraphylline, (D) IsoMitraphyllinee, (E) Uncarine C and (F) Uncarine E.
Figure 5:
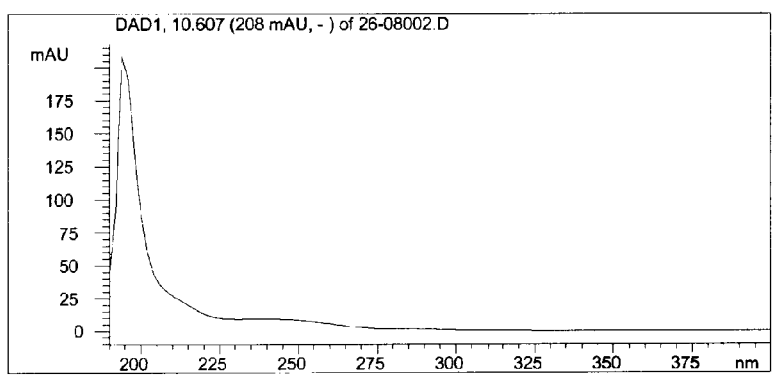
Figure 5:
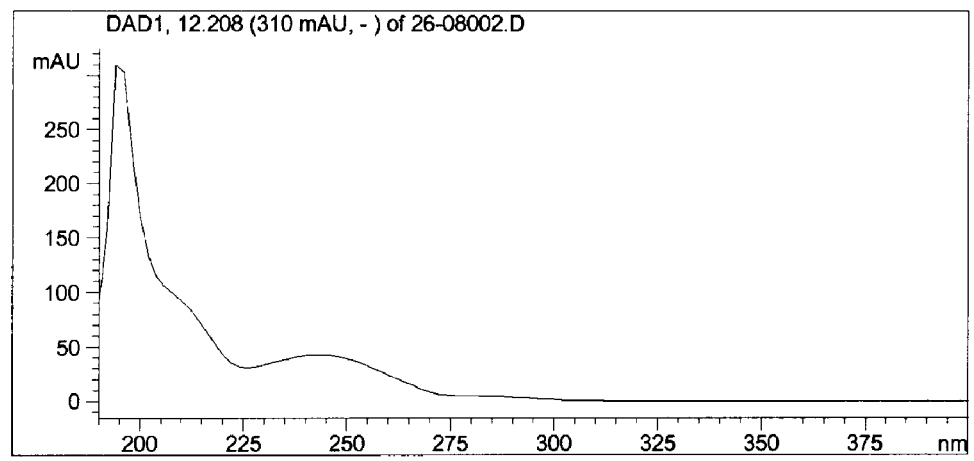
Figure 5:
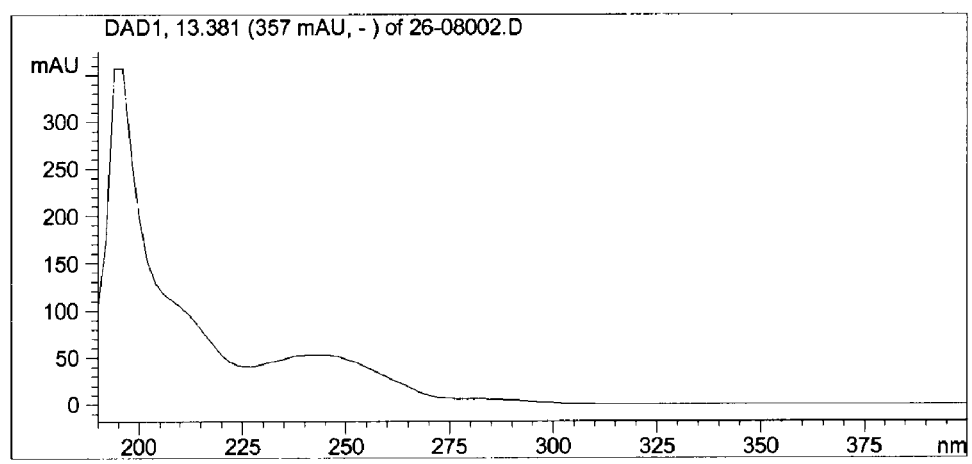
Figure 5:
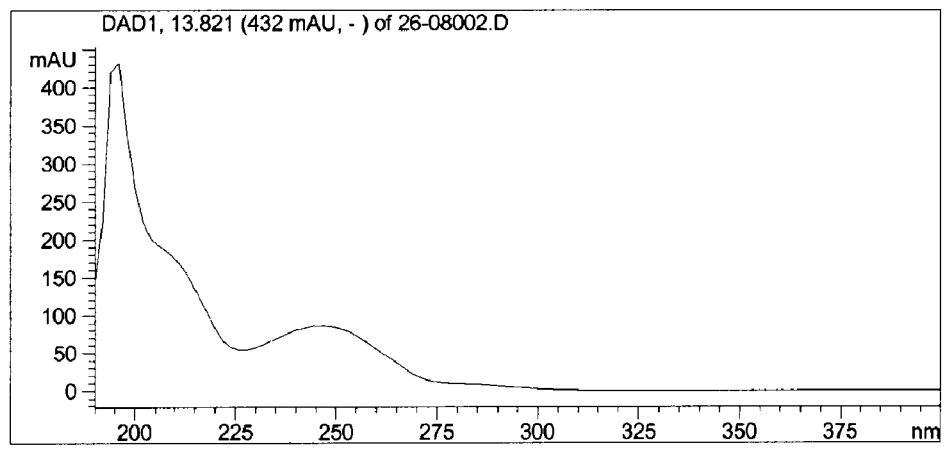
Figure 5:
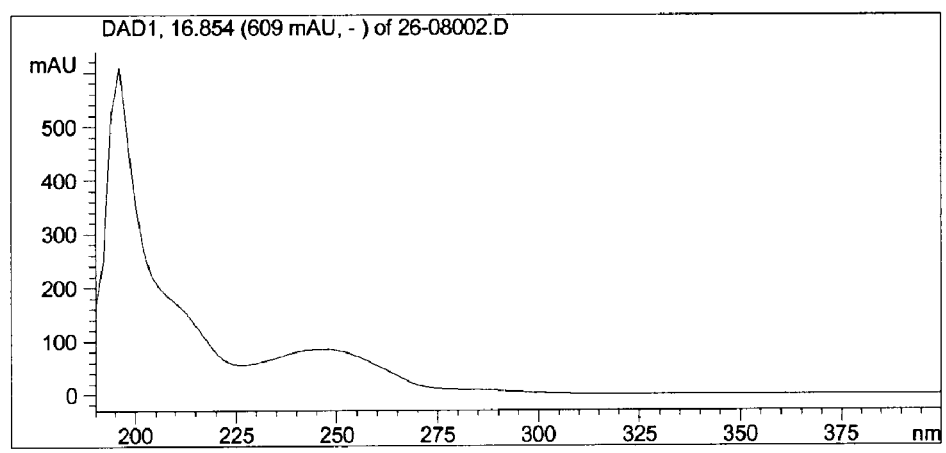

FIGS. 5A and B shows the qualitative analysis of the pentacyclic oxindole alkaloids included in the *Uncaria* tincture used in the most preferred compound of the present invention, here denominated Herbal Extract from *Uncaria tomentosa* (Willd) DC Rubiaceae. In the FIG. 5 (A) the tincture's chromatogram is presented. In the FIGS. 5 (B) through 5 (F) the spectrums of the tincture's constituents are presented: uncarine F, Mitraphyllinee, isoMitraphyllineee, uncarine C and uncarine E, respectively. The analysis has been performed in a High Efficiency Liquid Chromatograph assembled with a Diode Arrangement Detector (DAD).

Two parameters have been taken into consideration for the execution of the qualitative analysis of the *Uncaria tincture*'s alkaloids:

Comparison of the holding times of the pure standards of the alkaloids Mitraphyllinee, isoMitraphyllineee, uncarine C and uncarine E with the respective eluated peaks during the course of the *Uncaria tincture*.

Spectral Qualification of every Oxindole Alkaloid present in the *Uncaria tincture*'s chromatogram.

Figure 4:
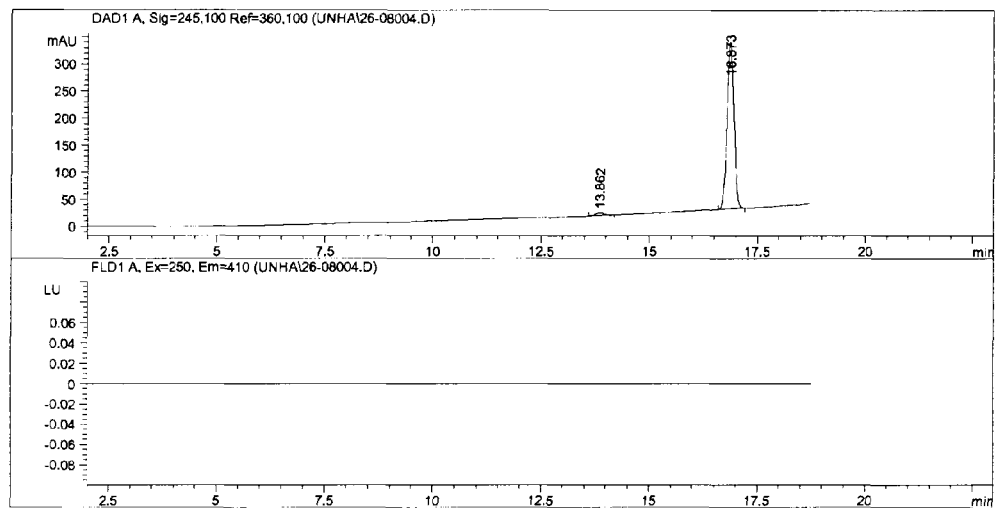
FIG. 4 shows the chromatogram (A) and the spectrum (B) of the Uncarine E standard ($t_r$=16.873), another pentacyclic oxindole alkaloid.
Figure 4:
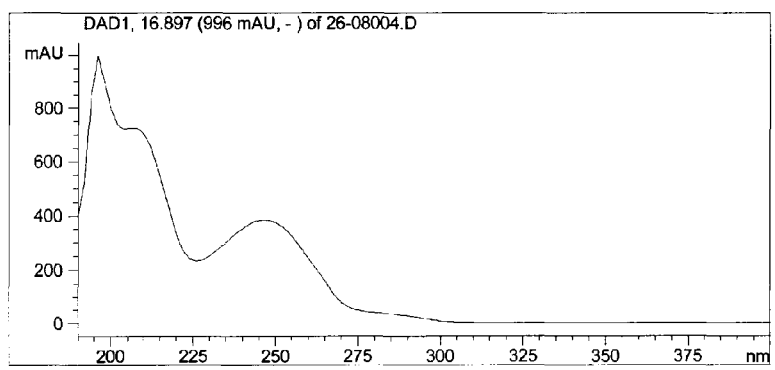

For comparison purposes, the FIGS. 1 through 4 illustrate the chromatograms and spectrums of the standards of: Mitraphyllinee, IsoMitraphyllineee, Uncarine C and Uncarine E, respectively. The chromatogram of the Mitraphyllinee standard shows the eluated peak in 12.290 (FIG. 1A), the IsoMitraphyllineee chromatogram in 13.382 (FIG. 2 A), the Uncarine C chromatogram has this compound's peak in 13.834 (FIG. 3 A), the Uncarine E chromatogram shows the peak in 16.873 (FIG. 4 A).

Compared to what is observed in the *Uncaria tincture*'s chromatogram, the alkaloids' holding times are shown to be: Mitraphylline: 12.251; IsoMitraphyllinee: 13.370; Uncarine C, 13.833; Uncarine E: 16.856. The closeness between the holding times is strongly indicative that the compounds are the same.

In addition to the holding times comparison between the alkaloids standards and the eluated peaks in the tincture's analysis, the comparison by similarity of the spectral profiles of the oxindole alkaloids in the standards and in the sample has been performed.

Such comparison has shown a great similarity between the spectrums of the standards and of the eluated compounds with the same holding time in the tincture. Therefore, a reasonably reliable conclusion can be made that the alkaloids present in the *Uncaria tincture* are the standards injected in the analysis.

Finally, the analysis of the purity factor of the peaks and of the asymmetry factor of the alkaloids' peaks in the tincture shows their purity and resolution.

The compound of the present invention is prepared by the mixture of the active ingredient herbal extract from *Uncaria tomentosa* (Willd) DC Rubiaceae with a pharmaceutically acceptable vehicle, resulting in a topical application product preferentially in the form of a cream gel.

The compound of the present invention, preferably in the form of a cream gel, contains one or more pharmaceutical excipients or vehicles. Such excipients or vehicles are selected from the substances known in the technical state and usually utilized for that purpose. At least one of the excipients or vehicles is a solvent of the used active ingredient, selected from the group which includes water; alcohols with a low molecular weight, preferably alcohols $C_1$ to $C_5$, more preferably ethanol, 2-propanol, isopropanol, t-butanol; ethers, such as the MTBE; ketones, such as acetone, methyl ethyl ketone. The compound of the invention contains as well: humectants, such as glycerol; glycols, such as ethylene glycol, propylene glycol; emulsifiers, such as the alcohols $C_1$ to $C_5$, optionally polyhydric partially esterified with long-chain fatty acids $C_{12}$ to $C_{24}$, such as glycerol monostearate, isopropyl myristate, sugar alcohols fatty acid ester, such as the sorbitan fatty acid monoester, polyoxyalkilate derivates of those compounds, polyetoxyethylene fatty acid ester, cholesterol, cetyl estearyl alcohol, cotton wax alcohols and synthetic tensoactive agents with a low HLB value; viscosity donors or rheology modifiers such as carbopol, or other polymers or synthetic or natural gums; low viscosity paraffins, emollient esters and alcohols, triglycerides, lipophilic substances such as isopropyl myristate or isopropyl palmnitate; pH regulators such as TEA, carbonates or phosphates; quelant agents such as EDTA and its salts, as well as preservatives, such as methylparaben and propylparaben; emollient agents such as oils or waxes of vegetal origin, such as the musk rose oil; antioxidants as BHT or other antioxidant mixtures.

Furthermore, the compound in form of gel of the present invention may contain substances with UV filter properties, pigments, vitamins and other adjuvants frequently used in compounds for topical application.

In a preferred concretization, the compound of the present invention is in the form of a hydrophilic cream gel, meaning it has an elevated water content (80-90%).

In an especially preferred concretization, the topical phytotherapic compound for the treatment of herpes presents the following composition: TABLE-US-00001 Herbal extract from *Uncaria tomentosa* 4.25-5.75% (Willd) DC Rubiaceae (active principle) Emulsifying compound (excipient) 3.4-4.6% Sorbitol esters derived from Colza Oil (*Brassica campestris*)—CAS 91081-14-0 Copolymer of the acryloyl-methyltaurate sulfonic acid and neutralized vinylpirrolidone—CAS 75-65-0 Citric Acid—CAS 77-92-9 Isopropyl palmitate—CAS 142-91-6 Tetradibutyl Pentaerythrityl Hydroxyhydrocinnamate 0.0425-0.0575% (excipient)—CAS 6683-19-8 Disodium EDTA (excipient)—CAS 139-33-3 0.085-0.115% Methylparaben (excipients)—CAS 99-79-3 0.17-0.23% Propylparaben (excipients)—CAS 94-13-3 1.1275-0.1725% Glycerin (excipients)—CAS 56-81-5 2.55-3.45% *Rosa Aff. Rubiginosa* oil (excipient) 2.125-2.875% Deionized water (vehicle) q.s. 100%.

This topical phytotherapic compound for the treatment of herpes results in a semi viscous cream gel product with a glossy aspect, salmon colored, with pH in a 4.8-5.8 range, and with dosing of total oxindole alkaloids calculated in Mitraphylline of 28-38 µg/g.

In the tests performed with the especially preferred compound of the present invention, the activities of the topical phytotherapic active substance for the treatment of herpes in nociception and inflammation models were studied; it was observed that, in the test of formalin-induced pain, the compound presented a significant antinoceptive activity at the second stage of the pain, with a 41.7% decrease in the pain threshold. Said composition has also presented a significant (36%) reduction of the oedema.

Such outcomes have confirmed that the compound of the present invention exerts a surprising analgesic effect on pain of inflammatory origin due to the release of inflammatory mediators such as histamine, serotonin, bradykinin and prostaglandins. In the characterization of its antioedematogenic activity, by means of the test of the caragenine-induced paw oedema, the compound caused a 11% decrease in such oedematogenic response, confirming its ability of oedema reduction. The compound of the invention has presented no significant antinoceptive effect in the test of capsaicin-induced neurogenic pain and in the Tail Flick test.

The compound of the present invention has confirmed its significant action in inhibiting the pain of inflammatory origin, with an anti-inflammatory efficiency of 87.2% compared to the 73.9% of the standard drugs known of the technical state.

The preferred compound is illustrative of the present invention, and it is worth noting that the components are combined and the amounts are represented in a percentage by weight, based on the total weight of the compound which contains the topical phytotherapic extract.

It is emphasized that the invention is not restricted to the preferred compound, and the invention should be understood in its ample scope. Many modifications and other representations of the invention may come to the mind of those skilled in the art, with the benefit of the information included in the description. Moreover, it should be understood that the present invention is not limited to the specifically disclosed content, and that eventual alterations should be taken as included within the scope of what is claimed ahead. Although specific terms have been utilized, they were used in a generic and descriptive way and not with a restrictive purpose.

What is claimed is:

1. A topical phytotherapic composition for the treatment of herpes, said composition comprising:
   (i) from about 4.25% to about 5.75% of herbal extract from *Uncaria tomentosa* (Willd) DC Rubiaceae;
   (ii) from 3.4% to 4.6% of an emulsifying agent selected from the group consisting of: sorbitol esters derived from colza oil (*Brassica campestris*); copolymer of acryloylmethyltaurate sulfonic acid; neutralized vinylpyrrolidone; citric acid; and isopropyl palmitate;
   (iii) from 0.0425% to 0.0575% of tetradibutyl pentaerythrityl hydroxyhydrocinnamate;
   (iv) from 0.085% to 0.115% of dissodic EDTA;
   (v) from 0.17% to 0.23% of methylparaben;
   (vi) from 1.1275% to 0.1725% of propylparaben;
   (vii) from 2.55% to 3.45% of glycerin;
   (viii) from 2.125% to 2.875% of Rosa *Aff. Rubiginosa* oil,
   (ix) deionized water q.s. 100%,
   (x) a pharmaceutically acceptable vehicle, and
   (xi) at least one pharmaceutically acceptable excipient.

2. The topical phytotherapic composition according to claim 1, wherein the herbal extract from *Uncaria tomentosa* (Willd) DC Rubiaceae:
   (a) has an appearance of a slightly turbid liquid;
   (b) has an acrid odor characteristic of *Uncaria tomentosa;*
   (c) has a reddish brown color;
   (d) has a dry residue of from 2.95% to 5.23%;
   (e) has a pH of from 5.0 to 5.5;
   (f) has a density of from 0.862 g/ml to 0.982 g/ml;
   (g) has a content of total pentacyclic oxindole alkaloids, calculated as mitraphyline, from about 660 µg/g to about 900 µg/g;
   (h) identification by thin layer chromatography with bands in RFs of about 0.7 to 0.8 and about 0.25 to 0.3 related to the alkoids, and
   (i) identification by HPLC chromatogram as described in FIG. 5(A).

3. The topical phytotherapic composition according to claim 1, wherein the at least one pharmaceutically acceptable vehicle is selected from the group consisting of: water; alcohols with molecular low weight; ethers; and ketones.

4. The topical phytotherapic composition according to claim 3, wherein the alcohols with molecular low weight of the at least one pharmaceutically acceptable vehicle is selected from the group consisting of: alcohols $C_1$ to $C_5$.

5. The topical phytotherapic composition according to claim 3, wherein the alcohols with molecular low weight of the at least one pharmaceutically acceptable vehicle is selected from the group consisting of: ethanol, 2-propanol, isopropanol, and t-butanol.

6. The topical phytotherapic composition according to claim 3, wherein the ether is MTBE.

7. The topical phytotherapic composition according to claim 3, wherein the ketone is selected from the group consisting of: acetone and methyl ethyl ketone.

8. The topical phytotherapic composition according to claim 1, wherein the at least one pharmaceutically acceptable excipient is selected from the group consisting of: humectants; glycols; emulsifiers; synthetic tensoactives with a low HLB value solubilizing agents, stable viscosity agents; low viscosity paraffins; emollient esters and alcohols; triglycerides; lipophilic substances; pH regulators; quelant agents; preservatives; emollient agents; and antioxidant agents.

9. The topical phytotherapic composition according to claim 8, wherein the humectant is a glycerol.

10. The topical phytotherapic composition according to claim 8, wherein the glycol is selected from the group consisting of: ethylene glycol and propylene glycol.

11. The topical phytotherapic composition according to claim 8, wherein the emulsifier is selected from the group consisting of: alcohols $C_1$ to $C_5$; polyhydric partially esterified with long-chain fatty acids $C_{12}$ to $C_{24}$, selected from the group consisting of: glycerol monostearate; isopropyl myristate; sugar alcohols fatty acid ester selected from the group consisting of: sorbitan fatty acid monoester, polyoxyalkilate derivates of those compositions, polyetoxyethylene fatty acid ester, cholesterol, cetyl estearyl alcohol, cotton wax alcohols; and synthetic tensoactive agents with a low HLB value.

12. The topical phytotherapic composition according to claim 8, wherein the stable viscosity agents are selected from the group consisting of: carbopol; polymers; synthetic gums; and natural gums.

13. The topical phytotherapic composition according to claim 8, wherein the lipophilic substance is selected from the group consisting of: isopropyl myristate and isopropyl palmitate.

14. The topical phytotherapic composition according to claim 8, wherein the pH regulator is selected from a group consisting of: TEA, carbonates, and phosphates.

15. The topical phytotherapic composition according to claim 8, wherein the quelant agent is EDTA or its salts.

16. The topical phytotherapic composition according to claim 8, wherein the preservative is selected from the group consisting of:

methylparaben and propylparaben.

17. The topical phytotherapic composition according to claim 8, wherein the emollient agent is selected from the group consisting of: *Rosa Aff. Rubiginosa* oil; similar oils of vegetal origin; and similar waxes of vegetal origin.

18. The topical phytotherapic composition according to claim 8, wherein the antioxidant agent is BHT or other suitable antioxidant mixtures.

19. The topical phytotherapic composition according to claim 1, wherein the composition is in the form of a cream gel.

20. The topical phytotherapic composition according to claim 1, wherein the composition is in the form of a semi viscous cream gel with a glossy aspect, having a pH from 4.8 to 5.8, and a total oxindolic alkaloid dosage calculated in mitraphylline of from about 28 µg/g to 38 µg/g.

21. The topical phytotherapic composition according to claim 20, wherein the composition in the form of a semi viscous cream gel is salmon colored.

\* \* \* \* \*